US008710106B2

(12) United States Patent
Junaedi et al.

(10) Patent No.: US 8,710,106 B2
(45) Date of Patent: Apr. 29, 2014

(54) SABATIER PROCESS AND APPARATUS FOR CONTROLLING EXOTHERMIC REACTION

(75) Inventors: Christian Junaedi, Cheshire, CT (US); Kyle Hawley, Woodbury, CT (US); Subir Roychoudhury, Madison, CT (US)

(73) Assignee: Precision Combustion, Inc., North Haven, CT (US)

( * ) Notice: Subject to any disclaimer, the term of this patent is extended or adjusted under 35 U.S.C. 154(b) by 355 days.

(21) Appl. No.: 13/134,966

(22) Filed: Jun. 22, 2011

(65) Prior Publication Data

US 2012/0029095 A1 Feb. 2, 2012

Related U.S. Application Data

(60) Provisional application No. 61/400,502, filed on Jul. 29, 2010.

(51) Int. Cl.
*C07C 27/00* (2006.01)
(52) U.S. Cl.
USPC ............................ 518/700; 518/705; 518/715
(58) Field of Classification Search
USPC .......................................... 518/700, 705, 715
See application file for complete search history.

(56) References Cited

U.S. PATENT DOCUMENTS

| | | | |
|---|---|---|---|
| 5,051,241 | A | 9/1991 | Pfefferle |
| 6,156,444 | A | 12/2000 | Smith et al. |
| 6,746,657 | B2 | 6/2004 | Castaldi et al. |
| 7,504,047 | B2 | 3/2009 | Castaldi et al. |

OTHER PUBLICATIONS

James T. Richardson, "Improved Sabatier Reactions for In Situ Resource Utilization on Mars Missions," UHCL/University of Houston, Y1999-2000-ISSO, pp. 84-86; www.isso.uh.edu/publications/A9900/pdf/rich84.pdf.
G. Alptekin, R. Copeland, S. DeVoss, J. Lind, F. Smith, "An Advanced CO2 Removal and Reduction System," SAE International (2004), 2004-01-2445.
G. Alptekin, B. Hitch, M. Dubovik, J. Lind, F. Smith, "Prototype Demonstration of the Advanced CO2 Removal and Reduction System," SAE International (2005), 2005-01-2862.
J.D. Holladay, K.P. Brooks, R. Wegeng, J. Hu, J. Sanders, S.Baird, "Microreactor Development for Martian In Situ Propellant Production," Catalysis Today, 120 (2007), 35-44.
K.P. Brooks, J. Hu, H. Zhu, R.J. Kee, "Methanation of Carbon Dioxide by Hydrogen Reduction using the Sabtier Process in Microchannel Reactors," Chemical Engineering Scence, 62 (2007), 1161-1170.
Jianli Hu, K.P. Brooks, J.D. Holladay, D.T. Howe, T.M. Simon, "Catalyst Development for Microchannel Reactors for Martian in Situ Propellant Production," Catalysis Today, 125 (2007), 103-110.
C. Junaedi, K. Hawley, D. Walsh, S. Roychoudhury, M.B. Abney, J.L. Perry, "Compact and Lightweight Sabatier Reactor for Carbon Dioxide Reduction," presented at the International Conference on Environmental Sciences (ICES), Jul. 17, 2011.

*Primary Examiner* — Jafar Parsa
(74) *Attorney, Agent, or Firm* — Marie F. Zuckerman

(57) ABSTRACT

A Sabatier process involving contacting carbon dioxide and hydrogen in a first reaction zone with a first catalyst bed at a temperature greater than a first designated temperature; feeding the effluent from the first reaction zone into a second reaction zone, and contacting the effluent with a second catalyst bed at a temperature equal to or less than a second designated temperature, so as to produce a product stream comprising water and methane. The first and second catalyst beds each individually comprise an ultra-short-channel-length metal substrate. An apparatus for controlling temperature in an exothermic reaction, such as the Sabatier reaction, is disclosed.

17 Claims, 5 Drawing Sheets

SABATIER PROCESS AND APPARATUS FOR CONTROLLING EXOTHERMIC REACTION

CROSS-REFERENCE TO RELATED APPLICATIONS

This application claims the benefit of U.S. provisional patent application Ser. No. 61/400,502, filed Jul. 29, 2010.

GOVERNMENT SUPPORT

This invention was made with support from the U.S. government under U.S. Contract No. NNX10CF25P sponsored by the National Aeronautics and Space Administration. The U.S. Government holds certain rights in this invention.

FIELD OF THE INVENTION

In one aspect, this invention pertains to a process of converting a mixture of carbon dioxide and hydrogen into a product mixture comprising water and methane (hereinafter "the process"). In the art the process is known as the "Sabatier process" or the "Sabatier reaction" or the "carbon dioxide methanation reaction." In another aspect, this invention pertains to an apparatus that finds use as a reactor for an exothermic process, for example, the Sabatier reaction.

BACKGROUND OF THE INVENTION

Currently, oxygen generators onboard the International Space Station produce oxygen by means of the electrolysis of water. Hydrogen, produced as a co-product of the electrolysis, is discarded overboard. Accordingly, large quantities of water are required to be transported to the Space Station, not only for the production of oxygen, but also for human consumption and other purposes, including hygiene. For long duration space missions at the Space Station or beyond low Earth orbit, the transportation of large amounts of water from Earth into space is prohibitive. Accordingly, water needed for the production of oxygen and other purposes must be supplied by a method other than transportation from Earth.

As astronauts consume oxygen through respiration, carbon dioxide is produced, which must be removed from the atmosphere within the Space Station or spacecraft designed for longer missions beyond Earth orbit. Currently, carbon dioxide generated in a spacecraft is removed by passing the cabin air through a bed of pelleted sorbent capable of adsorbing carbon dioxide. When the bed is saturated, it is regenerated by exposing the bed to space vacuum while heating the bed. The carbon dioxide that is liberated is then vented overboard. Clearly it would be beneficial to find a method of utilizing the carbon dioxide to produce life support consumables onboard of a spacecraft instead of venting the carbon dioxide overboard. Likewise, it would be beneficial to find a method for removing or utilizing carbon dioxide in extraterrestrial atmospheres that contain large quantities of carbon dioxide, for example, the Martian atmosphere.

Current interest is centered on the Sabatier reaction for in-situ resource utilization of carbon dioxide and for production of required human consumables, specifically, water and oxygen, for space missions. The Sabatier reaction specifically converts a mixture of carbon dioxide and hydrogen in the presence of a catalyst into a mixture of water and methane. The reaction accomplishes a primary goal of converting carbon dioxide, built-up in a space capsule or ubiquitous to an extraterrestrial environment, into valuable human consumables, specifically water, which is valued in itself or is converted into life-supporting oxygen. The Sabatier reaction eliminates the need to transport large quantities of water from Earth into space and, in this aspect, the Sabatier reaction reduces the payload projected from Earth and maintained on space voyages.

Methane resulting as a coproduct of the Sabatier reaction could be utilized advantageously as a propellant for a return voyage to Earth. On the other hand, methane is not easily compressed and stored in outer space; therefore, it may desirable to dump methane overboard or to convert methane into a high value liquid product, such as methanol, which is more readily stored.

The chemical equation for the Sabatier reaction for converting carbon dioxide and hydrogen into water and methane is presented in Equation 1:

$$CO_2 + 4H_2 \rightarrow 2H_2O + CH_4 \qquad \text{(Eqn. 1)}$$

The chemical equation representing the electrolysis of water to produce oxygen and hydrogen is represented in Equation 2:

$$2H_2O \rightarrow 2H_2 + O_2 \qquad \text{(Eqn. 2)}$$

Human respiration takes the oxygen so produced and converts it into carbon dioxide per Equation 3:

$$O_2 \xrightarrow{\text{Respiration}} CO_2 \qquad \text{(Eqn. 3)}$$

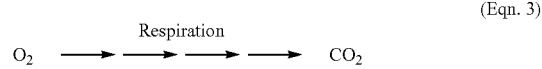

The overall process of Equations 1, 2, and 3 provides for a closed loop among water, oxygen, and carbon dioxide. On the other hand, whereas one-half (50 mole percent) of the hydrogen needed for the Sabatier reaction can be derived from the electrolysis of water, the remaining one-half (50 percent) of the hydrogen needed for the Sabatier reaction will need to be obtained from Earth or other sources. It might be desirable to obtain the balance of hydrogen from the pyrolysis of the methane coproduced in the Sabatier reaction, per Equation 4:

$$CH_4 + \text{heat} \rightarrow C + 2H_2 \qquad \text{(Eqn. 4)}$$

The Sabatier process is discussed by James T. Richardson in "Improved Sabatier Reaction for In Situ Resource Utilization on Mars Mission," published on-line in 1999-2000, at www.isso.uh.edu/publications/A9900/pdf/rich84.pdf. Richardson teaches the Sabatier reaction (1) over a catalyst comprising a pelleted bed of gamma-alumina having ruthenium deposited thereon, and alternatively (2) over a catalyst comprising a reticulated ceramic foam containing a gamma-alumina washcoat impregnated with ruthenium. Richardson notes that the Sabatier reaction is exothermic and subject to equilibrium conditions. He further teaches that above an operating temperature of 300° C., equilibrium conversions start to decrease.

The art also discloses a carbon dioxide removal and reduction system comprising a combination of a molecular sieve adsorbent bed for removing $CO_2$ from a space cabin environment and a Sabatier reactor to convert the adsorbed $CO_2$ into methane and water. See "An Advanced $CO_2$ Removal and Reduction System," by Gökhan Alptekin, et al., *SAE International*, 2004-01-2445 (2004), and "Prototype Demonstration of the Advanced $CO_2$ Removal and Reduction System," by Gokhan Alptekin, et al., *SAE International*, 2005-01-2862 (2005). The Sabatier section of the system is taught to be divided into a High Temperature Sabatier reactor and a Low Temperature Sabatier reactor, each one comprising a pelleted bed of catalyst in separate reactor housings. Both reactors are disclosed to be operated adiabatically.

Three publications disclose the Sabatier process using microchannel reactors for in-situ resource utilization of indigenous resources on Mars to produce hydrocarbon propellants. See the following: J. D. Holladay, K. P. Brooks, R. Wegeng, J. Hu, J. Sanders, and S. Baird in "Microreactor development for Martian in situ propellant productions," *Catalysis Today*, 120 (2007), 35-44; Kriston P. Brooks, Jianli Hu, Huanyang Zhu, and Robert J. Kee, "Methanation of carbon dioxide by hydrogen reduction using the Sabatier process in microchannel reactors," *Chemical Engineering Science*, 62 (2007), 1161-1170; and Jianli Hu, Kriston P. Brooks, Jamelyn D. Holladay, Daniel T. Howe, and Thomas M. Simon, "Catalyst development for microchannel reactors for Martian in situ propellant production," *Catalysis Today*, 125 (2007), 103-110. The referenced microchannel reactor comprises a series of rectangular channels, the walls of which are lined with a porous intermetallic alloy felt coated with a catalytic metal on metal oxide washcoat, for example, ruthenium on titania ($Ru-TiO_2$). The microchannel reactor further comprises a series of exterior channels through which an oil circulates countercurrently to the flow of the reactant gases, namely, carbon dioxide and hydrogen. Disadvantageously, the microchannel reactor provides for unacceptable heat transfer that leads to hot spots in the catalyst and catalyst deactivation. Moreover, the microchannel reactor provides an unacceptably high thermal mass and unacceptable mixing of reactant gasses between channels.

With respect to the above-identified art, a reactor bed of pelleted catalyst provides a disadvantageously large volume and payload mass for use in spacecraft. Having two or more pelleted bed reactor modules, as disclosed in Alptekin, et al., further negatively impacts the volume and weight of the system. More disadvantageously, beds of pelleted catalysts are prone to unacceptable heat transfer rates, sluggish transient response, and catalyst degradation over time, thereby rendering pelleted catalysts undesirable for space missions. A reactor based on a ceramic foam catalyst or the aforementioned microchannel design is disadvantageously limited to low throughputs due to a relatively high thermal mass. Additionally, local hot spots can occur in interior microchannels of the ceramic foam, which may facilitate catalyst deactivation.

Thus, while the utilization of carbon dioxide to produce life support consumables, such as water and oxygen, via the Sabatier reaction is an important aspect of the National Aeronautics and Space Administration's (NASA) Atmosphere Revitalization System (ARS) and In-Situ Resource Utilization (ISRU) concepts for low-earth orbit as well as long-term manned space missions, a need still exists in the art to find a compact, lightweight, and mechanically durable apparatus for the Sabatier process. The design is further challenged by the fact that the Sabatier reaction is highly exothermic (−165 kJ/mol). The art would also benefit from finding a catalyst for the Sabatier process that provides efficient conversion of carbon dioxide and excellent selectivity to water and methane with durability of catalyst performance. It would be more desirable if the apparatus and process were capable of operating at high throughputs and low operating temperatures while achieving essentially equilibrium conversion of carbon dioxide and equilibrium selectivity to water and methane.

SUMMARY OF THE INVENTION

In one aspect, this invention pertains to a novel two-stage Sabatier process of converting carbon dioxide into a mixture of water and methane. The novel Sabatier process comprises:
(a) contacting a mixture of carbon dioxide and hydrogen in a first reaction zone in the presence of a first catalyst bed comprising at least one layer of ultra-short-channel-length metal substrate, the contacting occurring at a temperature greater than a first designated temperature, so as to produce an effluent comprising water and methane and unconverted carbon dioxide and hydrogen; and
(b) contacting the effluent from step (a) in a second reaction zone with a second catalyst bed comprising at least one layer of ultra-short-channel-length metal substrate, the contacting occurring at a temperature equal to or less than a second designated temperature, so as to produce a product comprising water and methane with a carbon dioxide conversion greater than about 80 percent of an equilibrium carbon dioxide conversion under isothermal process conditions.

For the purposes of this invention, the term "carbon dioxide conversion" is defined as the moles of carbon dioxide changed to products in the overall two-stage process divided by the moles of carbon dioxide fed to the first reaction zone, on a percentage basis. The words "an equilibrium carbon dioxide conversion under isothermal process conditions" refers to the carbon dioxide conversion that is theoretically achievable at equilibrium, as calculated for an isothermal Sabatier process at a specified temperature, pressure, and inlet $H_2/CO_2$ mole ratio. The word "isothermal" refers to a process being operated and maintained at essentially one specified temperature at all points in the reaction section.

The process of this invention, which requires the use of an ultra-short-channel-length metal substrate and specific temperature control of each catalyst bed, advantageously achieves improved conversion of carbon dioxide, as compared with prior art processes using a pelleted catalyst bed or a microchannel ceramic foam catalyst. Specifically, where prior art microchannel reactors have been reported to yield up to 78.6 percent $CO_2$ conversion, at 350° C., a space velocity of 30,000 $hr^{-1}$, and a stoichiometric ratio of $H_2/CO_2$ (4/1), the process of the present invention under the same process conditions is able to achieve 90 percent $CO_2$ conversion as limited only by the equilibrium condition itself. More advantageously, use of the ultra-short-channel-length metal substrate provides for improved heat and mass transfer, which lead to improved carbon dioxide conversion and improved yields of water and methane. Even more advantageously, when using the temperature control described herein, the process of this invention, in preferred embodiments, achieves a near-equilibrium $CO_2$ conversion, that is, about 97 percent of the equilibrium $CO_2$ conversion at isothermal process conditions.

The ultra-short-channel-length catalysts used in the process of this invention operate at acceptably uniform temperatures close to the temperature of the reacting gasses. In contrast, catalysts of the prior art, such as pelleted beds or microchannel ceramic foams, are prone disadvantageously to hot spots that lead to catalyst degradation. For example, after 100 hours of operation, the $CO_2$ conversion demonstrated by the prior art catalyst supported on metal felt in a microchannel reactor is reduced from an initial value of approximately 70 percent to approximately 62 percent. In contrast, the catalyst in the process of this invention has been run for a similar duration at essentially equilibrium $CO_2$ conversion and essentially without indication of catalyst degradation.

In addition, the catalyst bed used in the process of this invention, comprising the ultra-short-channel-length metal substrate, is more compact and weighs appreciably less than prior art pelleted catalyst beds and prior art ceramic microchannel foam or metal catalysts. Thus, the process of this invention advantageously results in smaller launch payloads and lower launch costs. Moreover, the catalyst comprising the ultra-short-channel-length metal substrate of this invention exhibits improved mechanical durability, as compared with pelleted catalysts. One method of measuring mechanical durability involves weighing fines produced when the catalyst is exposed to vibrational stress. Mechanical durability is important where the catalyst is expected to withstand significant vibrational load, such as during launch into space.

In NASA's current spacecraft cabin concept, the waste methane produced by the Sabatier process is expected to be vented overboard resulting in a net loss of hydrogen. In order to obtain a maximum recovery of hydrogen, the coproduced methane could be separated and used as a propellant or converted to an easily stored liquid fuel, such as methanol. Thus, it is possible to integrate the Sabatier process of this invention with a gas-to-liquid (GTL) conversion process to convert methane to methanol. As a further alternative, it is possible to integrate the Sabatier process of this invention with a methane-to-hydrogen pyrolysis process, shown in Equation (4) hereinabove, in order to provide the balance of hydrogen needed for the Sabatier reaction.

In another aspect, this invention pertains to an apparatus for use in an exothermic reaction, the apparatus comprising:
(a) a first reaction zone containing a first catalyst bed comprising at least one layer of an ultra-short-channel-length metal substrate;
(b) a second reaction zone in fluid communication with and downstream from said first reaction zone, the second reaction zone containing a second catalyst bed comprising at least one layer of ultra-short-channel-length metal substrate;
(c) at least one inlet for feeding one or more reactants into the first reaction zone;
(d) an outlet for removing a product stream from said second reaction zone;
(e) a means for removing heat from said first reaction zone so as to maintain a temperature in said first reaction zone less than a maximum temperature suitable for materials of construction but greater than a first designated temperature; and
(f) a means for removing heat from said second reaction zone so as to maintain a temperature in said second reaction zone equal to or less than a second designated temperature.

The apparatus of this invention is especially advantageous for use in an exothermic process, where in a first temperature regime (i.e., at a first designated temperature) product formation is facilitated kinetically, and where in a second temperature regime (i.e., at a second designated temperature) product formation is facilitated thermodynamically. The term "kinetically" refers to the rate of change from initial to final states of the chemical process (i.e., reactants to products) under non-equilibrium conditions. The rate of change directly depends upon the driving force or potential and inversely depends upon resistance (activation energy). The term "thermodynamically" refers to the driving force or potential of a process derived from the equilibrium conditions of the initial and final states of the chemical process.

While the process and apparatus of this invention are described herein for use in space capsule and extraterrestrial applications, the invention is not limited thereto. The process and apparatus of this invention can be used advantageously to the benefit of both humans and animals in any confined environment where carbon dioxide build-up may become a problem including, for example, submarines and environmentally-controlled geodesic domes. Moreover, while the methane produced by the process of this invention has been described herein to be discarded, or used as a fuel, or converted to methanol, or pyrolyzed to recover hydrogen, it is to be understood that the methane so produced herein may be employed in any other downstream process that converts methane to a useful chemical or employs methane in a clean energy technology.

DRAWINGS

DETAILED DESCRIPTION OF THE INVENTION

Figure 1:
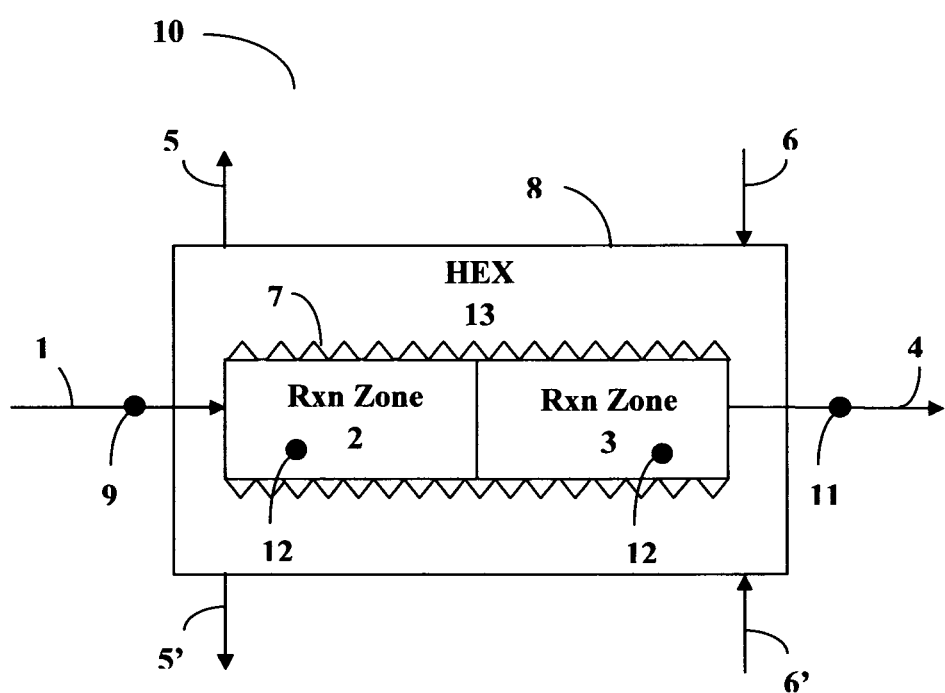
FIG. 1 depicts a first preferred embodiment of the apparatus of this invention.

In a preferred embodiment, this invention pertains to a novel two-stage Sabatier process of converting carbon dioxide and hydrogen into a mixture of water and methane, the process comprising:
(a) contacting a mixture of carbon dioxide and hydrogen in a first reaction zone in the presence of a first catalyst bed comprising at least one layer of ultra-short-channel-length metal substrate, the contacting occurring at a temperature greater than about 240° C., so as to produce an effluent comprising water and methane and unconverted carbon dioxide and hydrogen; and
(b) contacting the effluent from step (a) in a second reaction zone with a second catalyst bed comprising at least one layer of ultra-short-channel-length metal substrate, the contacting occurring at a temperature equal to or less than about 400° C., so as to produce a product comprising water and methane with a carbon dioxide conversion greater than about 80 percent of an equilibrium carbon dioxide conversion under isothermal process conditions.

Under the temperature conditions of the preferred embodiment, a carbon dioxide conversion is achieved that is preferably greater than about 80 mole percent, more preferably, greater than about 85 mole percent, and most preferably, greater than about 90 mole percent. Moreover, the selectivity to water and methane, as defined hereinafter, are each individually greater than about 90 mole percent.

In another preferred embodiment, this invention pertains to an apparatus for use in an exothermic process, comprising:
(a) two concentric tubular sections, such that an inner tube of a specified diameter is positioned within an outer tube of a larger diameter; the outer tube comprising a housing; the inner tube comprising a reactor section; and the annular space bounded by the inner tube and the outer tube comprising a heat exchange section;
(b) the reactor section comprising a first catalyst bed, and a second catalyst bed downstream and in fluid communication with the first catalyst bed; the first and second catalyst beds each individually comprising at least one layer of ultra-short-channel-length metal mesh substrate having one or more Group VIII metals deposited thereon;

(c) at least one inlet for feeding one or more reactants into the first catalyst bed;

(d) an outlet for removing a product stream from the second catalyst bed;

(e) at least one inlet for feeding a heat exchange fluid into the annular space between the inner tube and the outer tube, the inlet being coincident with the second catalyst bed; and (f) at least one outlet for removing the heat exchange fluid from the annular space between the inner tube and the outer tube, the outlet being coincident with the first catalyst bed.

In a more preferred embodiment, the apparatus of this invention is employed in an exothermic Sabatier process for converting carbon dioxide and hydrogen into a mixture comprising water and methane.

In another preferred embodiment, the apparatus further comprises a heat exchange unit comprising the following parts: (g) a tubular inlet portion passing from a location outside the outer tube, through the outer tube and the inner tube, into the reactor section of the inner tube, therein sequentially connected to (h) a tubular coiled portion positioned in a space between the first catalyst bed and the second catalyst bed, therein sequentially connected to (i) a tubular outlet portion passing from a location within the reactor section between the first and second catalyst beds, through the inner tube and through the outer tube to a location outside the outer tube. The preferred design provides for circulating a cooling fluid through the coiled tube, such that hot reaction gases exiting the first catalyst bed as an effluent stream are heat exchanged with the cooling fluid prior to such effluent stream entering the second catalyst bed.

In a more preferred embodiment of the above-described process and apparatus inventions, the first and second catalyst beds each individually comprise at least one layer of ultra-short-channel-length metal mesh having deposited thereon nickel, ruthenium, rhodium, or a combination thereof.

Reference is made to FIG. 1, which depicts a preferred embodiment 10 of the apparatus of this invention, comprising two concentric tubes including an outer tube forming housing 8, an inner tube of smaller diameter comprising a reactor section containing reaction zone 2 and reaction zone 3, and an annular space between the outer tube and the inner tube that forms a heat exchange section 13. A first inlet 1 is provided for feeding one or more reactants, such as carbon dioxide and hydrogen, to the first reaction zone 2 comprising a first catalyst bed. Downstream from said first reaction zone 2 and in fluid communication therewith lays second reaction zone 3 comprising a second catalyst bed. In this embodiment, the two reaction zones 2 and 3 are positioned sequentially in close proximity, meaning that there is essentially no gap between the first and second catalyst beds, which appear contiguous. Second reaction zone 3 is in fluid communication with outlet 4 for removing a product stream comprising one or more reaction products, for example water and methane, from the reactor. In this preferred embodiment, a plurality of heat exchange fins 7 are braised onto the exterior wall of reaction zones 2 and 3 for facilitating heat removal. Ports 5, 5', 6, and 6' are attached to the housing 8 so as to provide a flow path for a heat exchange fluid into and out of the annular space between the inner tube defining reaction zones 2 and 3 and the outer tube defining housing 8. The heat exchange fluid may be any conventional liquid or gaseous coolant, preferably, air. Heat exchange fluid flow may be operated concurrently with the flow direction of the reactants, such that the heat exchange fluid is fed into ports 5, and 5' and a warmer heat exchange fluid exits ports 6 and 6'. (Embodiment not shown in FIG. 1) Preferably, as shown in FIG. 1, the heat exchange fluid flows counter-current to the flow of reactants, such that the heat exchange fluid is fed into ports 6 and 6' and a warmer heat exchange fluid exits ports 5 and 5'. Thermocouples for measuring temperature can be attached at a plurality of locations on the apparatus, preferably, at location 9 along the inlet flow path, at location 11 along the exit flow path, and at one or more locations 12 in each of the reaction zones 2 and 3.

Figure 2:
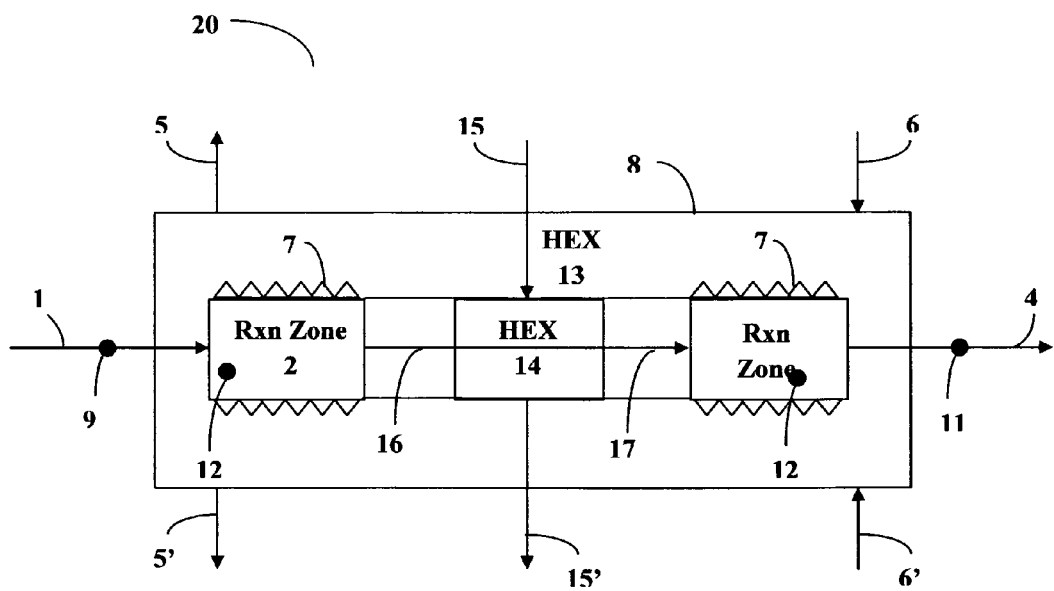
FIG. 2 depicts a second preferred embodiment of the apparatus of this invention.

Reference is made to FIG. 2, which depicts another embodiment 20 of the apparatus of this invention. Unit elements of this embodiment corresponding to the same unit elements of the apparatus shown in FIG. 1 are given identical reference numbers. Thus, the apparatus comprises two concentric tubes including an outer tube defining a housing 8 and an inner tube defining a reactor section comprising a first reaction zone 2 and a second reaction zone 3, and an annular space between the inner tube of the reactor section (2, 3) and the outer tube of housing 8, which forms a heat exchange section 13. A first inlet 1 is provided for feeding one or more reactants to the first reaction zone 2 comprising a first catalyst bed. Downstream from said first reaction zone 2 and in fluid communication therewith lays second reaction zone 3 comprising a second catalyst bed. In the embodiment of FIG. 2, the two reaction zones 2 and 3 are separated by a gap into which is located heat exchanger 14. Reaction zone 3 is in fluid communication with outlet 4 for removing a product stream comprising one or more products from reaction zone 3. In this preferred embodiment, a plurality of heat exchange fins 7 are braised onto the exterior wall of reaction zones 2 and 3 for facilitating heat removal. Ports 5, 5', 6, and 6' are attached to the housing 8 so as to provide a flow path for a heat exchange fluid into and out of the annular space between the inner tube defining reaction zones 2 and 3 and the outer tube defining the housing 8. The heat exchange fluid may be any conventional liquid or gaseous coolant as noted hereinabove. The heat exchange fluid flow may be operated concurrently or counter-currently with the flow direction of the reactants. FIG. 2 illustrates the preferred counter-current flow, wherein the heat exchange fluid is fed into ports 6 and 6' and a warmer heat exchange fluid exits ports 5 and 5'. Thermocouples for measuring temperature can be attached at a plurality of locations on the apparatus, preferably, at location 9 along the inlet flow path, at location 11 along the exit flow path, and at one or more locations 12 in each of the reaction zones 2 and 3. In the embodiment of FIG. 2, heat exchanger 14 comprises, for example, a tubular coil having an inlet port 15 and an exit port 15' passing through the housing 8 and the inner tube, and is positioned in the gap between reaction zone 2 and reaction zone 3 for the purpose of circulating heat exchange fluid through the tubular coil so as to provide additional cooling of effluent stream 16 exiting first reaction zone 2 prior to entry via inlet line 17 into second reaction zone 3.

In FIGS. 1 and 2, both reaction zones 2 and 3 are situated within one housing 8, which provides for a compact, lightweight apparatus and simple heat exchange design; but the invention is not limited to one housing. If not preferable, it is nevertheless possible to position each reaction zone 2 and 3 within a separate housing and to provide inlet and exit ports for heat exchange fluids to circulate as coolants around each separate catalyst bed within each separate housing.

The individual elements of the apparatus of this invention, including but not limited to the housing, reaction zones, catalyst substrates, inlets, outlets, and any other conduits or attachments, can be constructed from any material capable of withstanding the temperature at which the unit element is operated. Suitable materials of construction include stainless steel, alloys of appropriate temperature durability, and high temperature steels, wherein the term "high temperature" refers to steels that are able to withstand a temperature up to 1250° C.

The first and second catalyst beds each individually comprise an ultra-short-channel-length metal substrate having deposited thereon one or more catalytic metals active in the Sabatier process. Preferably, the catalytic metal or metals are selected from the Group VIII metals of the Periodic Table, including iron, cobalt, nickel, ruthenium, rhodium, palladium, osmium, iridium, platinum, or a combination thereof. More preferably, the catalytic metal or metals are selected from nickel, ruthenium, rhodium, or a combination thereof. The catalysts may, if desired, be supported on an oxide support, preferred species of which include, without limitation, titania ($TiO_2$, e.g., anatase and rutile phases), silica ($SiO_2$), magnesia (MgO), alumina ($Al_2O_3$), zirconia ($ZrO_2$), and mixtures thereof. The catalytic metal or metals, either unsupported or supported on a metal oxide support, are bound to an ultra-short-channel-length metal substrate. While the ultra-short-channel-length metal substrate is not limited to any particular structure, the substrate is preferably supplied as a metal mesh that comprises a reticulated screen or net containing a plurality of void spaces or ultra-short-channels. A preferred configuration comprises a stack or plurality of metal mesh sheets piled or layered in an essentially orderly fashion one against the other. From 2 to about 300 metal mesh sheets or layers are preferred. It is also possible to use one extended metal mesh sheet or layer rolled upon itself in a coiled cylindrical configuration. The metal may comprise any metal or alloy that can withstand the Sabatier process conditions, including but not limited to stainless steel, iron-based alloys, and nichrome (a nickel chromium alloy optionally containing iron).

Ultra-short-channel-length metal substrates suitable for catalytic purposes are commercially available, for example, from Alpha Aesar and Petro Wire & Steel. In a most preferred embodiment, the substrate comprises a Microlith® brand ultra-short-channel-length metal mesh substrate obtained from Precision Combustion, Inc., of North Haven, Conn., USA. Microlith® brand ultra-short-channel-length metal mesh substrate technology, described for example in U.S. Pat. No. 5,051,241 and U.S. Pat. No. 6,156,444, incorporated herein by reference, is a unique catalyst design comprising ultra-short-channel-length, low thermal mass metal monoliths that contrast with prior art monoliths having long channel lengths. For the purposes of this invention, the term "ultra-short-channel-length" refers to channel lengths in a range from about 25 microns (μm) (0.001 inch) to about 500 μm (0.02 inch). In contrast, the term "long channels" pertaining to prior art monoliths refers to channel lengths from about 1 mm (0.039 inch), preferably, greater than about 5 mm (0.20 inch). Thus, while prior art monoliths are three-dimensional structures having long flow paths running there through; in contrast, the ultra-short-channel-length metal mesh substrate comprises a reticulated screen or net having an ultra-short flow path. When two or more ultra-short-channel-length metal mesh screens are stacked or when one extended sheet of ultra-short-channel-length metal mesh is rolled to form a coil, the resulting configurations each comprise a plurality of void volumes in random order. The term "void volumes" refers to the empty spaces between the metallic elements or strands from which the mesh is constructed. The term "random order" refers to an absence of regular arrangement or periodicity.

As compared with prior art monolithic catalysts, the ultra-short-channel-length metal mesh substrate facilitates packing more active surface area into a smaller volume and provides increased reactive area for a given pressure drop. Whereas in prior art honeycomb monoliths having conventional long channels, a fully developed boundary layer is present over a considerable length of the channels; in contrast, the ultra-short-channel-length characteristic of the substrate of this invention avoids boundary layer buildup. Since heat and mass transfer coefficients depend on boundary layer thickness, avoiding boundary layer buildup enhances transport properties. The advantages of employing the ultra-short-channel-length metal substrate, and preferably, the Microlith® brand thereof, to control and limit the development of a boundary layer of a fluid passing there through is described in U.S. patent application Ser. No. 10/832,055, now granted as U.S. Pat. No. 7,504,047, which is a Continuation-In-Part of U.S. Pat. No. 6,746,657 to Castaldi, both patents incorporated herein by reference.

The one or more Group VIII metals, in the form of elemental metal or metal ions, are deposited onto the ultra-short-channel-length metal substrate. A typical Group VIII metal loading ranges from about 125 milligrams per cubic inch (125 mg/in$^3$) to about 375 mg/in$^3$ (from about 7.6 to about 22.9 mg/cm$^3$). Prior to use, the Group VIII metal thusly deposited onto the metal substrate is subjected to reduction under a hydrogen-containing atmosphere, for example, a stream of pure hydrogen or a gaseous mixture containing hydrogen and a non-reactive gas, such as nitrogen or argon. Advantageously, the reduction is conducted at a temperature ranging from about 400° C. to about 800° C. for a time ranging from about 15 minutes to about 3 hours.

The resulting catalyst comprising the ultra-short-channel-length substrate having one or more Group VIII metals deposited thereon has been found to have a higher mechanical durability, as compared with a catalyst prepared by analogous methods using conventional pelleted supports. For purposes of this invention, mechanical durability is based on durability of adhesion of the Group VIII metal to the substrate. Improved mechanical durability is important, especially if the catalyst is intended to withstand the vibrations encountered on launch into space.

Mechanical durability can be evaluated by a simple testing procedure developed by the inventors, details of which are described hereinafter. Specifically, an aluminum plate (12"×12") is supported on vibration isolation mounts. To simulate launch vibration loads, vibration of the plate is excited by use of an industrial grade pneumatic vibrator (circulating ball style) mounted in the center of the plate. An acceptable average peak force is about 50 times that of gravity (50 gs) over the test time. An acceptable vibration frequency is about 250 Hz, but other vibration frequencies may be chosen. The catalyst comprising the ultra-short-channel-length substrate having the catalytic metal(s) deposited thereon is placed in a pre-weighed plastic bag, which is then zip-closed. The loaded plastic bag is attached to the plate and vibrated for a total of about 40 to 80 minutes. The quantity of catalyst lost through vibration is collected in the plastic bag and weighed. Typically, for the catalyst comprising the ultra-short-channel-length substrate used in this invention, the weight loss was found to be typically less than about 0.2 weight percent, the weight loss being based on the amount of "fines" generated relative to the weight of total catalytic metal and washcoat, but exclusive of the weight of the metal substrate. The percentage loss might be significantly higher when excluding the weight of the substrate; which means that the value of 0.2 weight percent observed for the catalyst used in this invention is likely to be an upper limit.

Carbon dioxide ($CO_2$) for use in the process of this invention can be obtained from any source including, but not limited to, human respiration, byproducts of industrial processes, oxidation processes, Earth's atmosphere, extraterrestrial atmospheres, space station or space capsule environments, submarine environments, or any combination thereof. In respect of NASA's Aircraft Resource Utilization program targeting space travel, carbon dioxide will be provided by respiration of human subjects residing within a space capsule. A carbon dioxide collection system is likely to be needed to concentrate and/or purify the carbon dioxide prior to its use in the Sabatier process. In particular, it is advantageous to separate the carbon dioxide from oxygen, because the presence of oxygen in the Sabatier process leads to loss of valuable hydrogen through oxidation to water. It is not required, however, to separate carbon dioxide from nitrogen, although it may be desirable to do so. Nitrogen dilutes the carbon dioxide, so reactor capacity may need to be increased if a large quantity of nitrogen is present in the carbon dioxide feed. Moreover, under some process conditions, the nitrogen may waste hydrogen by reaction to form ammonia. Still, a small amount of nitrogen may be desirable, for example, as an internal standard for analytical purposes.

Hydrogen ($H_2$) is a required co-reactant in the process of this invention. Any source of hydrogen is suitably employed, provided that the hydrogen is sufficiently pure, by which we mean that the hydrogen has a purity preferably greater than about 95 mole percent. The hydrogen may be obtained from any suitable source. Preferably, the hydrogen is obtained from synthesis gas, fuel reforming, petroleum cracking, pyrolysis of methane, electrolysis of water, or a combination thereof.

Oxygen desirably comprises less than about 10 volume percent, preferably, less than about 1 volume percent, and more preferably less than about 0.1 volume percent, of the total reactant feed to the Sabatier process including carbon dioxide, hydrogen, oxygen, and any other gasses. On the other hand, nitrogen and inert gases, such as helium, neon, and argon, may be present in a quantity greater than about 10 volume percent without substantively affecting the catalytic reaction. For example, a nitrogen or inert gas concentration up to about 40 volume percent can be employed, if desired. Generally, however, the presence of nitrogen or an inert gas dilutes the reactants, leading to either a required increase in reactor volume or increase in throughput in order to maintain an acceptable carbon dioxide conversion and water generation.

The hydrogen and carbon dioxide are fed to the first reaction zone in any operable inlet hydrogen to carbon dioxide ($H_2/CO_2$) mole ratio. Referring to Equation 1 hereinabove, a stoichiometric inlet ratio for complete consumption of carbon dioxide and hydrogen requires 4 moles of hydrogen per mole of carbon dioxide ($H_2/CO_2=4/1$). Nevertheless, the process can also be run with a variety of "rich" or "lean" mixtures, wherein the term "rich" refers to an inlet $H_2/CO_2$ mole ratio greater than 4/1 and the term "lean" refers to an inlet $H_2/CO_2$ mole ratio less than 4/1. If a rich mixture is used, then preferably, the inlet $H_2/CO_2$ mole ratio is greater than about 4.3/1, but preferably less than about 6.0/1. If a lean mixture is used, then preferably, the inlet $H_2/CO_2$ mole ratio is less than about 3.8/1, but preferably greater than about 2.0/1. Thus, the preferred inlet $H_2/CO_2$ mole ratio ranges overall from about 2/1 to about 6/1.

The catalysts employed in this invention advantageously provide for high throughput. The gas hourly space velocity (GHSV) of total reactants including total of carbon dioxide and hydrogen fed to the process is preferably greater than about 20,000 ml total reactants per ml catalyst bed per hour (20,000 $hr^{-1}$), and more preferably, greater than about 50,000 $hr^{-1}$. The GHSV is preferably less than about 250,000 $hr^{-1}$, and more preferably, less than about 70,000 $hr^{-1}$. Such throughputs allow for contact times between the reactant gases and the catalyst comprising the ultra-short-channel-length substrate on the order of about 14 milliseconds (ms) to about 180 ms. Process pressure in the first and second reaction zones can be maintained at any operable pressure ranging from sub-atmospheric to super-atmospheric. It is preferred to operate each reaction zone at roughly the same pressure in a range from about 0.5 atm (50.7 kPa) to about 10 atm (1013 kPa).

The prior art teaches that the Sabatier process can be operated adiabatically, wherein no heat is removed from the reaction zone and wherein reaction temperature increases along the length of the reactor. Alternatively, conventional process engineering allows for operating the Sabatier process isothermally, wherein heat is removed from the reaction zone, and wherein the entire reaction zone is maintained at a designated temperature. In the overall process of this invention, as explained hereinbelow, the process is neither adiabatic nor completely isothermal.

Figure 3:
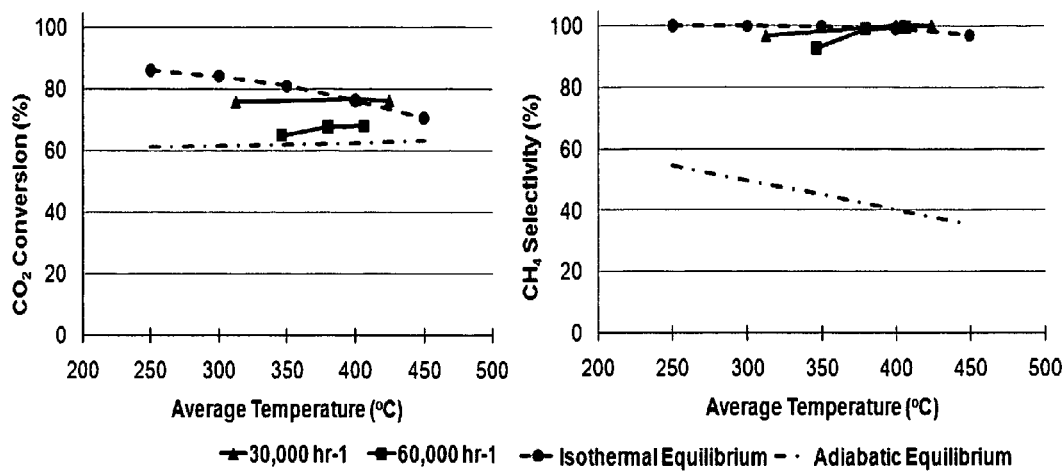
FIG. 3 depicts graphs of carbon dioxide conversion and methane selectivity of an embodiment of the process of this invention employing a rhodium catalyst and a $H_2/CO_2$ mole ratio of 3.5/1.
Figure 4:
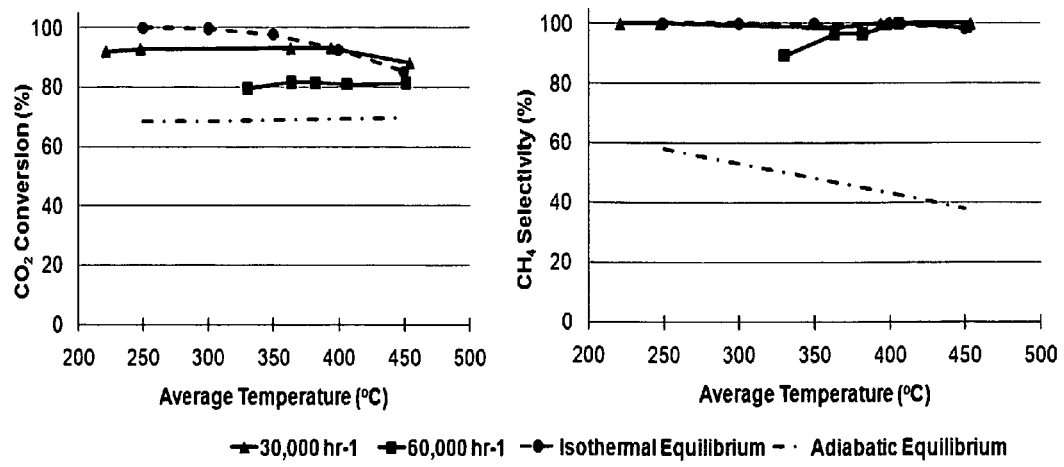
FIG. 4 depicts graphs of carbon dioxide conversion and methane selectivity of an embodiment of the process of this invention employing a rhodium catalyst and a $H_2/CO_2$ mole ratio of 4.0/1.
Figure 5:
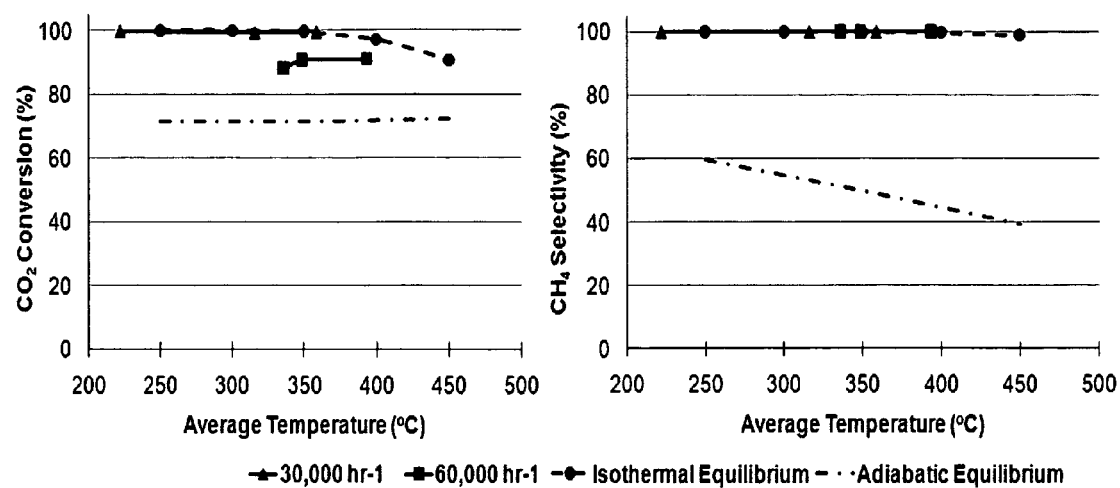
FIG. 5 depicts graphs of carbon dioxide conversion and methane selectivity of an embodiment of the process of this invention employing a rhodium catalyst and a $H_2/CO_2$ mole ratio of 5.5/1.

The Sabatier process is highly exothermic and therefore limited by thermodynamic equilibrium. The skilled process engineer will know how to calculate the thermodynamic equilibrium concentrations of water and methane in the product stream as a function of selected reactant feed and process conditions. Based on the composition of the reactant feed stream and the equilibrium composition of the product stream, the skilled person can readily calculate the equilibrium $CO_2$ conversion and the equilibrium selectivity to methane and water. A detailed thermodynamic calculation using ASPEN® software was performed by the inventors in order to evaluate the equilibrium product composition, the equilibrium $CO_2$ conversion, and the equilibrium $CH_4$ selectivity expected at a range of operating temperatures and inlet $H_2/CO_2$ mole ratios. The inlet temperature of the incoming reactants was taken in a range from 250° C. to 450° C., and the inlet $H_2/CO_2$ mole ratio was taken in a range from 2.5/1 to 5.0/1. Table 1 lists the predicted equilibrium $CO_2$ conversion and $CH_4$ selectivity at 1 atmosphere and process conditions as shown. FIGS. 3-5 graph the predicted equilibrium $CO_2$ conversion and $CH_4$ selectivity for the relevant inlet $H_2/CO_2$ mole ratio.

TABLE 1

Predicted Equilibrium $CO_2$ Conversion and $CH_4$ Selectivity
(at 1 atm and process conditions shown)

| $H_2/CO_2$ Ratio | Inlet Temperature (° C.) | $CO_2$ Conversion (mole %) | | $CH_4$ Selectivity (mole %) | |
|---|---|---|---|---|---|
| | | Isothermal | Adiabatic | Isothermal | Adiabatic |
| 3.5/1 | 250 | 86.1 | 61.2 | 99.99 | 54.4 |
| | 300 | 84.2 | 61.6 | 99.96 | 49.7 |
| | 350 | 81.0 | 62.1 | 99.8 | 45.0 |
| | 400 | 76.3 | 62.6 | 99.2 | 40.2 |
| | 450 | 70.5 | 63.3 | 97.1 | 35.1 |
| 4.0/1 | 250 | 97.5 | 65.1 | 100.00 | 56.1 |
| | 300 | 94.9 | 65.4 | 99.99 | 51.3 |
| | 350 | 90.9 | 65.7 | 99.9 | 46.5 |
| | 400 | 85.2 | 66.2 | 99.5 | 41.7 |
| | 450 | 78.3 | 66.8 | 97.9 | 36.8 |

TABLE 1-continued

Predicted Equilibrium $CO_2$ Conversion and $CH_4$ Selectivity
(at 1 atm and process conditions shown)

| $H_2/CO_2$ Ratio | Inlet Temperature (°C.) | $CO_2$ Conversion (mole %) | | $CH_4$ Selectivity (mole %) | |
|---|---|---|---|---|---|
| | | Isothermal | Adiabatic | Isothermal | Adiabatic |
| 5.5/1 | 250 | 100.00 | 71.47 | 100.00 | 59.74 |
| | 300 | 99.98 | 71.47 | 100.00 | 54.78 |
| | 350 | 99.67 | 71.62 | 99.99 | 49.72 |
| | 400 | 97.18 | 71.91 | 99.86 | 44.61 |
| | 450 | 90.70 | 72.31 | 98.96 | 39.49 |

Generally, it was found that $CO_2$ and $H_2$ conversions increased in all cases as temperature decreased. Moreover, $CO_2$ and $H_2$ conversions and $CH_4$ selectivity were found to be highest for the isothermal case. In contrast, the data indicated that the adiabatic conversion and selectivity were lower as compared with the isothermal case, which emphasizes the importance of temperature control for removing heat from the process. On the other hand, at operating temperatures below about 350° C., achieving equilibrium conversion and selectivity is a challenge, because the Sabatier reaction is kinetically limited. Thus, in order to achieve close to equilibrium conversions, a conventional reactor must either have a high active catalyst surface area per unit volume or must operate at a very low space velocity (i.e., long residence time). Either way, a conventional prior art approach results in a large catalyst volume and reactor size, both of which are unsuitable for payloads launched on space missions.

The challenge of achieving high conversions at low average temperatures (<about 400° C.), high throughputs, and with acceptable reactor volume has now been overcome by the inventors by running the process in a manner that is neither adiabatic nor strictly isothermal. Rather, the first reaction zone is advantageously maintained at a temperature less than a maximum temperature suitable for materials of construction but greater than a first designated temperature; while the second reaction zone is advantageously maintained at a temperature equal to or less than a second designated temperature. The phrase "at a temperature less than a maximum temperature suitable for materials of construction" refers to the highest temperature that the reactor section can be safely operated taking into consideration the materials from which the reactor section is constructed. The term "first designated temperature" refers to a temperature range within which product formation, for example carbon dioxide conversion and yields of water and methane, are improved by process kinetics. For the Sabatier process of this invention, preferably, the first reaction zone is maintained at a first designated temperature greater than 240° C. More preferably, for the Sabatier process the first reaction zone is maintained at a first designated temperature greater than about 300° C., and most preferably, greater than about 400° C. Advantageously, for the Sabatier process the first reaction zone is maintained at a maximum temperature less than about 600° C. The term "second designated temperature" refers to a temperature range within which product formation, for example carbon dioxide conversion and yields of water and methane, are improved by process thermodynamics. For the Sabatier process of this invention, preferably, the second reaction zone is maintained at a second designated temperature equal to or less than about 400° C., more preferably, equal to or less than about 350° C. Preferably, the second designated temperature is greater than about 100° C. An overall average temperature for the process can be calculated by averaging the temperatures of the first and second reaction zones.

Process temperature is measured using standard commercial thermocouples, preferably, attached to the surface of the catalyst in the first catalyst bed and to the surface of the catalyst in the second catalyst bed. By using a high process temperature in the first reaction zone, the kinetics of the Sabatier process drives the process toward high carbon dioxide conversion. By using a lower process temperature in the second reaction zone, the process is driven towards the equilibrium water and methane formation, which is the maximum achievable. In small-scale embodiments of the apparatus of this invention, the first and second designated temperatures can be maintained by manual adjustment of the flow rate of the heat exchange fluid. In commercial embodiments of the apparatus of this invention, the apparatus will further comprise a controller and feedback loop for monitoring the temperatures in the first and second catalyst beds and thereafter automatically adjusting the flow rate of the heat exchange fluid based on the differences between the temperatures measured and the selected designated first and second temperatures. As general guidance, when the temperature of the second catalyst bed exceeds the second designated temperature, then the flow rate of the heat exchange fluid is typically increased; whereas when the temperature of the first catalyst bed is lower than the first designated temperature, then the flow rate of the heat exchange fluid is typically decreased.

The product stream exiting the first reaction zone comprises water, methane, unconverted carbon dioxide, and unconverted hydrogen, and may further comprise carbon monoxide. The product stream exiting the second reaction zone will depend upon the inlet $H_2/CO_2$ mole ratio employed in the feed to the first reaction zone as well as the equilibrium composition at the process conditions employed. Under lean conditions wherein the $H_2/CO_2$ mole ratio is less than 4/1, the product stream exiting the second reaction zone typically consists essentially of water, methane, and unconverted carbon dioxide, and may further comprise carbon monoxide and slight amounts of unconverted hydrogen. Under rich conditions wherein the $H_2/CO_2$ mole ratio is greater than 4/1, the product stream exiting the second reaction zone consists essentially of water, methane, and unconverted hydrogen.

In the process of this invention, the carbon dioxide conversion is greater than about 80 percent, more preferably greater than about 85 percent, and most preferably, greater than about 90 percent of the equilibrium carbon dioxide conversion at isothermal process conditions. More specifically, the carbon dioxide conversion is advantageously greater than about 80 mole percent, preferably, greater than about 85 mole percent, and more preferably, greater than about 90 mole percent, based on the moles of carbon dioxide fed to the first reaction zone. In the process of this invention, the overall selectivity to methane and water is each individually greater than about 90 mole percent, preferably, greater than about 95 mole percent, and more preferably, greater than about 98 mole percent. "Selectivity to methane" is defined for these purposes as the moles of methane produced relative to the moles of carbon dioxide converted in the overall process, expressed as a percentage. Likewise, "selectivity to water" is defined herein as the moles of water produced relative to the moles of carbon dioxide converted in the overall process, expressed as a percentage. Insofar as is currently known, the process can be operated for up to about 100 hours without evidence of catalyst degradation.

The following examples are provided to illustrate the invention, but are not intended to limit the invention in any manner. In view of the description herein, an ordinary person skilled in the field will understand that equivalent components of the catalyst and apparatus and equivalent process parameters may be interchanged with those components and process parameters illustrated in the Examples; and that all such equivalent interchanges fall within the description and intention of the invention.

EMBODIMENTS OF THE INVENTION

Example 1

With reference to FIG. 1, a reactor 10 was constructed from stainless steel for use in the Sabatier process. The apparatus comprised two concentric tubes. A tube of larger diameter formed housing 8; an inner tube of smaller diameter provided a reactor section of two sequentially connected reaction zones 2 and 3. An annular space between the inner tube reactor section (2, 3) and the outer tubular housing 8 provided heat exchange section 13. A first inlet 1 was provided for feeding a mixture of carbon dioxide and hydrogen into the first reaction zone 2 comprising a first catalyst bed consisting of 15 layers of ultra-short-channel-length metal mesh substrate stacked one layer against the next layer. A second reaction zone 3 was positioned sequentially downstream of the first reaction zone 2. The second reaction zone 3 comprised 165 layers of ultra-short-channel-length metal mesh substrate, also stacked one layer against the next layer. The ultra-short-channel-length metal mesh substrates in catalyst beds 2 and 3 were each a Microlith® brand ultra-short-channel-length metal mesh substrate obtained from Precision Combustion, Inc., North Haven, Conn. Each catalyst was prepared by washcoating the layers of ultra-short-channel-length metal mesh substrate with alumina and then impregnating the washcoated substrate with rhodium (287 mg/in$^3$ (17.5 mg/cm$^3$)). The Rh—Al$_2$O$_3$ impregnated substrate was then reduced in a hydrogen atmosphere at 500° C. for 1 hour.

Reaction zone 3 was connected to outlet line 4 for removing a product stream from the reactor. A plurality of heat exchange fins 7 were braised onto the exterior wall of reaction zones 2 and 3 for facilitating heat removal. Ports 6, 6', 5, and 5' connected to housing 8 were provided for feeding and removing a heat exchange fluid into the annular space 13 between the inner tubular reaction zones 2 and 3 and the outer tubular housing 8. The heat exchange fluid was air, operated by flowing ambient temperature air into the heat exchange section via ports 6 and 6' and exiting hotter air from the heat exchange section via ports 5 and 5'. The flow of heat exchange fluid was countercurrent to the flow of carbon dioxide and hydrogen within the reactor. Thermocouples for measuring temperature were attached at location 9 along the inlet flow path, at location 11 along the exit flow path, and at locations 12 in each of the reaction zones 2 and 3.

The overall reactor section (2, 3) without the heat exchanger was 20.3 cm (8 inches) in length and 2.54 cm (1 inch) in diameter. The housing 8 with the heat exchanger had a diameter of 11.2 cm (4.4 inches). The braised fins 7 provided an additional 330 square inches (2,129 cm$^2$) of additional surface area for cooling. Reaction zones 2 and 3 contained only 11 grams of catalyst and substrate and took up only 12 ml of volume, which is believed to be sufficient for a 3.5-crewmember space capsule.

A pre-mixing region consisting of quartz beads was inserted upstream of catalyst bed 2 to ensure uniform mixing of the carbon dioxide and hydrogen. The reactant mixture in a specified inlet H$_2$/CO$_2$ mole ratio was pre-heated to a temperature of 500° C. and fed through inlet 1 and contacted with the first catalyst bed in reaction zone 2. The process was operated at atmospheric pressure; the space velocity of the combined reactant feeds of carbon dioxide and hydrogen was either 30,000 hr$^{-1}$ or 60,000 hr$^{-1}$ as indicated in the Tables hereinbelow. The Sabatier reaction commenced and given its exothermicity, the temperature of the first reaction zone 2 rose to a temperature greater than 240° C. The reaction gases exited first reaction zone 2 and flowed into the second reaction zone 3; and a product stream comprising methane and water and any unconverted carbon dioxide and/or hydrogen exited through outlet 4. Air, used as a coolant, was flowed into ports 6 and 6' into the heat exchanger, exiting at ports 5 and 5'. By so doing, the temperature of the second reaction zone 3 was maintained below 400° C.

The outlet gas composition was analyzed by on-line gas chromatography using a micro-gas chromatograph equipped with a thermal conductivity detector. Specifically, the outlet gas composition was analyzed for methane, carbon dioxide, hydrogen, nitrogen, and any side-product carbon monoxide. Nitrogen was introduced upstream of the reaction zone 2 or 3 as an internal standard for determining mass balance, CO$_2$ conversion, and CH$_4$ selectivity. The apparatus did not include a means to condense and analyze for the water formed. Nevertheless, according to the known stoichiometric equation, two moles of water will form for every mole of methane produced; and therefore, the water produced can be calculated from the observed yield of methane.

The process was initially operated at an H$_2$/CO$_2$ mole ratio of 3.5/1, a space velocity of 30,000 hr$^{-1}$, and at a sweep of average temperatures ranging from 300° C. to 450° C., with the results tabulated in Table 2 and illustrated in FIG. 3. The "average temperature" was determined by taking the operating temperatures of the first and second reaction zones (catalyst bed 2 and catalyst bed 3, respectively) and averaging them together.

The process was repeated, with the exception that the space velocity was increased to 60,000 hr$^{-1}$ with the results shown in Table 2 and FIG. 3.

TABLE 2

Sabatier Process Using Rh-Microlith ® brand ultra-short-channel-length substrate and H$_2$/CO$_2$ = 3.5/1

| Space Velocity (hr$^{-1}$) | T (° C.) Catalyst Bed 2 | T (° C.) Catalyst Bed 3 | Average T (° C.) | CO$_2$ Conversion (mole %) | CH$_4$ Selectivity (mole %) |
|---|---|---|---|---|---|
| 30,000 | 330.0 | 295.0 | 312.5 | 75.8 | 96.8 |
|  | 542.0 | 259.0 | 400.5 | 76.8 | 100.0 |
|  | 557.0 | 292.0 | 424.5 | 76.3 | 100.0 |
| 60,000 | 293.0 | 400.0 | 346.5 | 64.9 | 92.6 |
|  | 394.0 | 366.0 | 380.0 | 67.8 | 99.0 |
|  | 459.8 | 353.0 | 406.4 | 67.9 | 99.6 |

Example 2

The process of Example 1 was repeated, with the exception that the inlet H$_2$/CO$_2$ mole ratio was increased to 4.0/1. Results are tabulated in Table 3 and graphed in FIG. 4.

TABLE 3

Sabatier Process Using Rh-Microlith ® brand
ultra-short-channel-length substrate and H$_2$/CO$_2$ = 4.0/1

| Space Velocity (hr$^{-1}$) | T (° C.) Catalyst Bed 2 | T (° C.) Catalyst Bed 3 | Average T (° C.) | CO$_2$ Conversion (mole %) | CH$_4$ Selectivity (mole %) |
|---|---|---|---|---|---|
| 30,000 | 216.0 | 226.0 | 221.0 | 92.1 | 100.0 |
| | 257.5 | 238.0 | 247.8 | 92.9 | 100.0 |
| | 521.5 | 205.0 | 363.3 | 93.1 | 98.5 |
| | 536.5 | 252.0 | 394.3 | 93.3 | 100.0 |
| | 560.5 | 348.0 | 454.3 | 88.1 | 100.0 |
| 60,000 | 286.0 | 374.0 | 330.0 | 79.5 | 89.2 |
| | 380.0 | 348.0 | 364.0 | 81.6 | 96.4 |
| | 414.5 | 350.0 | 382.3 | 81.5 | 96.5 |
| | 476.0 | 337.0 | 406.5 | 80.9 | 100.0 |
| | 561.5 | 324.0 | 442.8 | 82.9 | 100.0 |
| | 555.5 | 347.0 | 451.3 | 81.4 | 98.7 |

Example 3

Example 1 was repeated, with the exception that the H$_2$/CO$_2$ mole ratio was increased to 5.5/1, with the results shown in Table 4 and in FIG. 5.

TABLE 4

Sabatier Process Using Rh-Microlith ® brand
ultra-short-channel-length substrate and H$_2$/CO$_2$ = 5.5/1

| Space Velocity (hr$^{-1}$) | T (° C.) Catalyst Bed 2 | T (° C.) Catalyst Bed 3 | Average T (° C.) | CO$_2$ Conversion (mole %) | CH$_4$ Selectivity (mole %) |
|---|---|---|---|---|---|
| 30,000 | 242.5 | 202.0 | 222.3 | 99.8 | 100.0 |
| | 347.8 | 284.5 | 316.1 | 99.3 | 100.0 |
| | 520.5 | 197.0 | 358.8 | 99.6 | 100.0 |
| 60,000 | 287.5 | 384.0 | 335.8 | 88.2 | 100.0 |
| | 378.5 | 319.0 | 348.8 | 90.8 | 100.0 |
| | 469.3 | 317.5 | 393.4 | 90.9 | 100.0 |

Example 4

Figure 6:
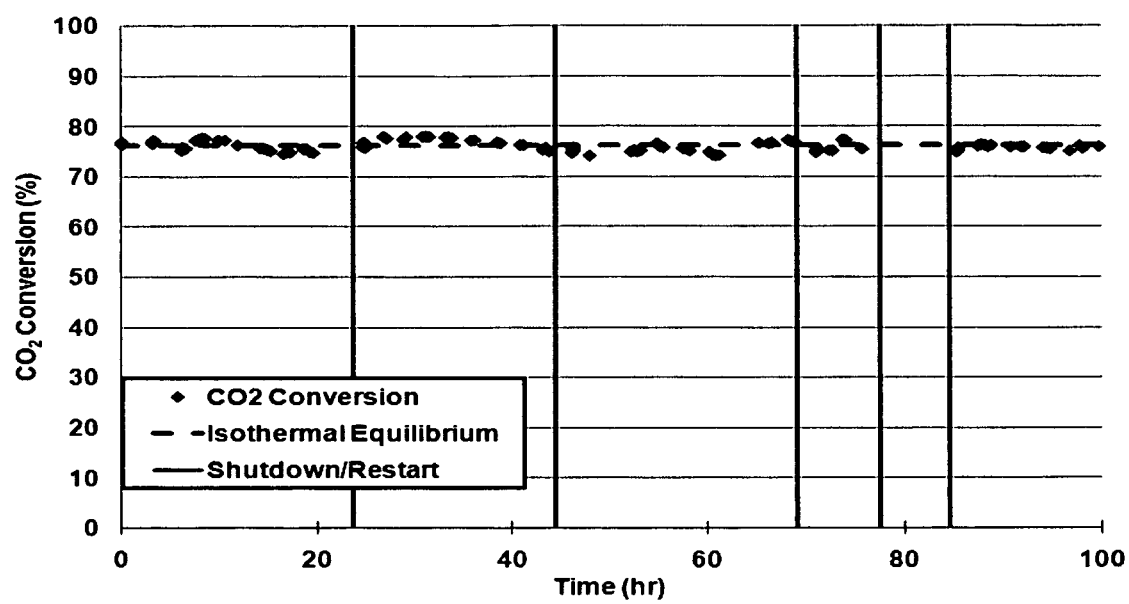
FIG. 6 depicts a graph of carbon dioxide conversion versus time of an embodiment of the process of this invention employing a rhodium catalyst.

A fresh catalyst comprising rhodium deposited on Microlith® brand ultra-short-channel-length metal mesh substrate (287 mg/in$^3$ (17.5 mg/cm$^3$)), prepared as in Example 1, was tested for its performance durability in a Sabatier process in accordance with the apparatus and experimental design of Example 1 hereinabove. Operating conditions: inlet H$_2$/CO$_2$=3.5/1; reactant partial pressure, 13.2 psi; gas hourly space velocity, 30,000 hr$^{-1}$; average temperature, 400° C., for an initial CO$_2$ conversion of 77 mole percent. Over the course of the 100 hour run, the catalyst was subjected to 5 startup/shutdown sequences in order to evaluate if this would put additional strain on the catalyst that might lead to unacceptable degradation. Results are shown in FIG. 6, where it is seen that the process ran for 100 hours with essentially equilibrium conversion of carbon dioxide. No degradation of the catalyst was observed despite several startup and shutdown operations.

The invention claimed is:

1. A process of converting a mixture of carbon dioxide and hydrogen into a mixture of water and methane, comprising:
(a) contacting a mixture of carbon dioxide and hydrogen in a first reaction zone in the presence of a first catalyst bed comprising at least one layer of ultra-short-channel-length metal substrate, the contacting occurring at a temperature greater than a first designated temperature, so as to produce an effluent comprising water and methane and unconverted carbon dioxide and hydrogen; and
(b) contacting the effluent from step (a) in a second reaction zone with a second catalyst bed comprising at least one layer of ultra-short-channel-length metal substrate, the contacting occurring at a temperature equal to or less than a second designated temperature, so as to produce a product comprising water and methane with a carbon dioxide conversion greater than about 80 percent of an equilibrium carbon dioxide conversion under isothermal process conditions.

2. The process of claim 1 wherein the carbon dioxide is obtained from human respiration, byproducts of industrial processes, oxidation processes, Earth's atmosphere, extraterrestrial atmospheres, space station or space capsule environments, submarine environments, or a combination thereof.

3. The process of claim 1 wherein the hydrogen is obtained from synthesis gas, fuel reforming, petroleum cracking, pyrolysis of methane, electrolysis of water, or a combination thereof.

4. The process of claim 1 wherein the hydrogen and carbon dioxide are fed to the first reaction zone in an inlet H$_2$/CO$_2$ mole ratio ranging from 2/1 to 6/1.

5. The process of claim 1 wherein the process is operated at a gas hourly space velocity (GHSV) of total reactants comprising carbon dioxide and hydrogen in a range greater than 20,000 hr$^{-1}$ and less than 250,000 hr$^{-1}$.

6. The process of claim 1 wherein the first and second reaction zones are maintained each individually at a pressure ranging from 0.5 atm (50.7 kPa) to 10 atm (1013 kPa).

7. The process of claim 1 wherein the ultra-short-channel-length metal substrate has channel lengths ranging from 25 microns (μm) (0.001 inch) to 500 μm (0.02 inch).

8. The process of claim 1 wherein the first and second catalyst beds each individually comprise an ultra-short-channel-length metal mesh substrate having deposited thereon one or more Group VIII metals.

9. The process of claim 1 wherein the first and second catalyst beds each individually comprise a linear stack of metal mesh substrates ranging in number from 2 to about 300 layers, each stack having a plurality of void volumes in random order.

10. The process of claim 1 wherein the first and second catalyst beds each individually comprise a coiled configuration of metal mesh substrate, the coil having a plurality of void volumes in random order.

11. The process of claim 1 wherein the first reaction zone is maintained at a first designated temperature greater than 240° C. and the second reaction zone is maintained at a second designated temperature equal to or less than 400° C.

12. The process of claim 1 wherein the first reaction zone is maintained at a first designated temperature greater than 300° C. and less than 600° C., and the second reaction zone is maintained at a second designated temperature equal to or less than 350° C. but greater than 100° C.

13. The process of claim 1 wherein the conversion of carbon dioxide is greater than 80 mole percent, based on the moles of carbon dioxide fed to the first reaction zone.

14. The process of claim 1 wherein the selectivity to methane and water are each individually greater than 80 mole percent, based on the moles of carbon dioxide converted to products.

15. The process of claim 1 wherein the methane produced is converted to methanol.

16. The process of claim 1 wherein the methane produced is pyrolyzed to produce hydrogen; and wherein the hydrogen is recycled to the first or second reaction zones.

17. The process of claim 1 comprising:
(a) contacting a mixture of carbon dioxide and hydrogen in a first reaction zone in the presence of a first catalyst bed comprising at least one layer of ultra-short-channel-length metal mesh substrate having one or more Group VIII metals deposited thereon, the contacting occurring at a temperature greater than 240° C. but less than 600° C., so as to produce an effluent comprising water and methane and unconverted carbon dioxide and hydrogen; and
(b) contacting the effluent from step (a) in a second reaction zone with a second catalyst bed comprising at least one layer of ultra-short-channel-length metal mesh substrate having one or more Group VIII metals deposited thereon, the contacting occurring at a temperature equal to or less than 400° C. but greater than 100° C., so as to produce a product comprising water and methane with a carbon dioxide conversion greater than 85 percent of an equilibrium carbon dioxide conversion under isothermal process conditions.

\* \* \* \* \*